United States Patent
Gross et al.

(10) Patent No.: US 8,786,283 B2
(45) Date of Patent: Jul. 22, 2014

(54) WHOLE-BODY COIL ARRANGEMENT FOR AN OPEN MAGNETIC RESONANCE SCANNER FOR USE WITH A SECOND DIAGNOSTIC AND/OR THERAPEUTIC MODALITY

(75) Inventors: Patrick Gross, Langensendelbach (DE); Bela Vajko, Shaker Heights, OH (US)

(73) Assignee: Siemens Aktiengesellschaft, Munich (DE)

( * ) Notice: Subject to any disclaimer, the term of this patent is extended or adjusted under 35 U.S.C. 154(b) by 456 days.

(21) Appl. No.: 12/858,663

(22) Filed: Aug. 18, 2010

(65) Prior Publication Data

US 2011/0043207 A1 Feb. 24, 2011

(30) Foreign Application Priority Data

Aug. 24, 2009 (DE) .......................... 10 2009 038 686

(51) Int. Cl.
*G01V 3/00* (2006.01)
(52) U.S. Cl.
USPC ........................................................ 324/318
(58) Field of Classification Search
USPC ................................................ 324/300–322
See application file for complete search history.

(56) References Cited

U.S. PATENT DOCUMENTS

| | | | | |
|---|---|---|---|---|
| 5,485,087 A | * | 1/1996 | Morich et al. | 324/318 |
| 5,834,687 A | * | 11/1998 | Talbot et al. | 174/386 |
| 6,249,121 B1 | * | 6/2001 | Boskamp et al. | 324/318 |
| 6,466,018 B1 | | 10/2002 | Dumoulin et al. | |
| 6,522,142 B1 | * | 2/2003 | Freundlich | 324/315 |
| 6,591,128 B1 | * | 7/2003 | Wu et al. | 600/422 |
| 2006/0273795 A1 | | 12/2006 | Rieke et al. | |
| 2011/0012593 A1 | * | 1/2011 | Shvartsman et al. | 324/307 |
| 2011/0118588 A1 | * | 5/2011 | Kornblau et al. | 600/411 |

FOREIGN PATENT DOCUMENTS

| | | |
|---|---|---|
| DE | 102006037047 A1 | 2/2008 |
| GB | 2424281 A * | 9/2006 |

OTHER PUBLICATIONS

Fahrig et al., "A Truly Hybrid Interventional MR/X-Ray System: Feasibility Demonstration", Journal of Magnetic Resonance Imaging, 2001, pp. 294-300, vol. 13, Wiley-Liss, Inc.

* cited by examiner

*Primary Examiner* — Melissa Koval
*Assistant Examiner* — Daniel Miller

(57) ABSTRACT

A whole-body coil arrangement for an open magnetic resonance scanner for use with a second diagnostic and/or therapeutic modality is proposed. The whole-body coil arrangement includes at least one coil conductor and a radio-frequency shield. The whole-body coil arrangement is embodied at least in part as essentially transparent to the second modality.

11 Claims, 1 Drawing Sheet

WHOLE-BODY COIL ARRANGEMENT FOR AN OPEN MAGNETIC RESONANCE SCANNER FOR USE WITH A SECOND DIAGNOSTIC AND/OR THERAPEUTIC MODALITY

CROSS REFERENCE TO RELATED APPLICATIONS

This application claims priority of German application No. 10 2009 038 686.6 filed Aug. 24, 2009, which is incorporated by reference herein in its entirety.

FIELD OF THE INVENTION

The invention relates to a whole-body coil arrangement for an open magnetic resonance scanner for use with a second diagnostic and/or therapeutic modality, comprising at least one coil conductor and a radio-frequency shield. The invention also relates to an associated magnetic resonance scanner and an associated combination device.

BACKGROUND OF THE INVENTION

Combination devices, by means of which both magnetic resonance imaging and the simultaneous use of a second diagnostic and/or therapeutic modality are possible, are desirable in many application areas. Combinations of magnetic resonance scanners with X-ray equipment, nuclear medicine equipment (PET, SPECT) or radiotherapy equipment (for irradiating a tumor, for example) shall be cited only by way of example. If a second modality of said kind is to be combined with a magnetic resonance scanner, a great problem is the structure of the magnetic resonance scanner per se.

A simplification in terms of the structural embodiment of combination devices came with the introduction of what are referred to as open magnetic resonance scanners, in which there is a greater accessibility to the patient. In particular an embodiment in which two essentially cylindrical and/or rectangular coaxial magnet sections are used, the so-called double-doughnut configuration, is particularly suitable for allowing appropriate access to a second modality. For example, in a double-doughnut configuration, if the patient is positioned along the z-axis through the openings of the two "doughnuts", access is possible in the axial plane between the two "doughnuts" or magnet sections.

One of the biggest challenges in this case is that the normally used cylindrical whole-body coils comprise a radio-frequency shield which essentially prevents, or at least severely restricts, the integration of a second modality, since the described access is blocked. Such whole-body coil arrangements are needed, however, on account of their outstanding properties, in particular with regard to susceptibility to failure.

Essentially three variants have been proposed in the past in order to solve the problem of unrestricted access to the patient: Firstly, the energy source and/or the detectors of the second modality can be disposed inside the whole-body coil arrangement. This, however, results in the considerable drawback that a very narrow structure exists and the introduced components of the second modality often affect the radio-frequency performance of the whole-body coil (and also of the gradients) and vice versa. In a second possible alternative it has been proposed to introduce the energy of the energy source through the two bores of the cylindrical or essentially cylindrical tunnel of the whole-body coil arrangement. This is not possible in all cases, since leads for the corresponding type of energy are not available or not compatible with the magnet resonance environment. Finally, it has also been proposed no longer to use a whole-body coil at all, though this results in a heavy loss of the field homogeneity and the robustness of the overall system.

In U.S. Pat. No. 6,466,018 B1 it has been proposed to use a birdcage coil without a radio-frequency shield. To ensure the coil conductors likewise do not create a disruptive influence, in that case with regard to the access to the patient, it has been proposed to embody the body coil as rotating, such that basically it can be rotated so that access to the patient is made possible. Due the absence of the radio-frequency shield, however, the magnetic resonance measurement is severely disrupted, and furthermore a costly and complex rotator device must be provided.

SUMMARY OF THE INVENTION

The object underlying the invention is therefore to disclose a whole-body coil arrangement for an open magnetic resonance scanner which, while having good shielding properties, nevertheless allows access to the patient by a second modality.

In order to achieve this object it is provided according to the invention in the case of a whole-body coil arrangement of the kind cited in the introduction that the body coil arrangement is embodied at least in part as essentially transparent to the second modality. With particular advantage the whole-body coil arrangement can in this case be embodied as transparent at least in the open portion of the magnetic resonance scanner; in particular it is embodied as essentially completely transparent.

Such an embodiment of the whole-body coil arrangement permits the second modality finally to be operated through the "walls" of the whole-body coil arrangement, for which reason it is proposed to embody at least the relevant parts of the whole-body coil arrangement as transparent with regard to the second modality. The medium used for measurement or treatment by the second modality, in other words, for example, electromagnetic radiation, particle radiation or waves, in particular ultrasound waves, can penetrate the relevant parts of the whole-body coil arrangement to the necessary extent.

Finally, it is therefore proposed to embody a whole-body coil arrangement as essentially transparent instead of actually open so that a radio-frequency shield can continue to be used. Consequently no disadvantages occur due to influences of conducting or dielectric structures in the vicinity of the radio-frequency coil. A further advantage of the essentially closed external surface of the whole-body coil arrangement according to the invention is its suitability for manufacture and its mechanical stability.

In this case the whole-body coil arrangement can be of arbitrary design, a so-called birdcage coil with end rings, for example, can be used just as well as configurations without end rings, for example TEM array body coils or whole-body coils having a plurality of conductor loops. This flexibility in the physical structure of the coil conductor is additionally supported by the inventive transparency that is given, in particular with regard to the radio-frequency shield.

The concrete embodiment of the transparency is in this case greatly dependent on the choice of the second modality per se. Various diagnostic and/or therapeutic devices are conceivable as the second modality, in particular an X-ray device and/or a nuclear medicine device and/or an ultrasound device and/or an optical examination apparatus operating in the visible range and/or an irradiation device.

In a further advantageous embodiment of the present invention it can be provided that the attenuation properties of the radio-frequency coil arrangement are homogenous in the transparent area. The measurement or treatment medium used by the second modality is consequently attenuated essentially uniformly in the transparent areas of the whole-body coil arrangement, with the result that no artifacts can occur due to different influencing factors, for example shadow impact. In this instance it can be provided, for example, if a carrier element is provided, to configure the carrier element as correspondingly somewhat thicker in areas in which no coil conductor is present, or alternatively to accommodate the coil conductor in recesses.

Preferably the coil conductor and/or the radio-frequency shield can be constructed from thin metal layers whose thickness is chosen taking into account in particular the penetration depth. The at least one coil conductor and/or the radio-frequency shield therefore form thin layers applied onto a carrier element, for example. It is well-known that coil conductors cannot be dimensioned arbitrarily thinly without this resulting in a strong increase in resistance. It is, however, conceivable, since the current conduction is essentially limited to edge zones of the conductor cross-section, to use thin layers in order to create geometric shapes which can exhibit excellent conducting properties. For example, two thin layers arranged in parallel in particular on a carrier can be connected by means of thin layers in order for example to create a square cross-section which for stabilization purposes can be filled with a material of extremely low density, for example cellular material. However, other embodiments are also conceivable in order to keep the layer thickness of the thin metal layers as low as possible and at the same time to provide a maximum of transparency, in particular with regard to electromagnetic radiation, for example X-ray radiation, or particle radiation, in particular beta radiation. Such layers can be applied using well-known methods, by means of sputtering, for example.

With particular advantage the coil conductor and/or the radio-frequency shield can consist of aluminum. Aluminum is characterized in that it exhibits excellent high conductivity, which is still maintained even in the case of thin layers.

In another advantageous embodiment of the present invention it can be provided that the radio-frequency shield is embodied at least in part as a fine-meshed grid ("mesh"). In this case there is a saving in terms of material in addition, while at the same time very good shielding properties are realized nonetheless. In particular it is even conceivable in the case of fine-meshed grids which can be applied by way of masks, for example, to achieve an optical transparency in the visible range. This can be combined particularly advantageously with a carrier element that is likewise optically transparent in the visible range, made, for example, out of a transparent plastic.

As already mentioned, it can be provided that the whole-body coil arrangement includes at least one thin carrier element, in particular made of plastic. Said carrier element can be used as a base for thin metal layers for the radio-frequency shield and/or the at least one coil conductor, and is itself embodied as essentially transparent, which is possible owing to the lower density or specific material properties. Transparency to diagnostic and/or therapeutic ultrasound can also be achieved by way of a special embodiment of the carrier element if at least one carrier element is embodied as a membrane coated with the radio-frequency shield. The membrane can consequently transfer the ultrasound.

The whole-body coil arrangement is preferably embodied as essentially cylindrical. It can then be used with particular advantage in a magnetic resonance scanner having the double-doughnut combination referred to in the introduction, i.e. in a magnetic resonance scanner comprising two essentially cylindrical and/or rectangular coaxial magnet sections. The normally open area between the magnet sections is then in fact covered by the whole-body coil arrangement, although since this is transparent to the second modality it can be used through the whole-body coil arrangement between the magnet sections.

Let it be pointed out at this juncture that the whole-body coil arrangement can, of course, also comprise elements which due to their nature (dependent, naturally, on the second modality) cannot be embodied as transparent, for example circuitry components such as capacitors or diodes. If these non-transparent elements are also present in areas in which a use of the second modality enters into consideration, then the whole-body coil arrangement can be mounted so as to be rotatable by way of a corresponding rotator device, such that non-transparent elements of this kind can be removed from the sphere of influence of components of the second modality.

In addition to the whole-body coil arrangement the present invention also relates to an open magnetic resonance scanner having a whole-body coil arrangement according to the invention. The use of a second modality with such an open magnetic resonance scanner is possible particularly easily. All statements made with regard to the whole-body coil arrangement can be applied analogously to the magnetic resonance scanner and to the combination device that is still to be discussed later.

In this case it can be provided in a further embodiment that the, in particular cylindrical, whole-body coil arrangement is mounted so as to be rotatable. In this way any elements of the whole-body coil arrangement that may be present and are embodied or can be embodied as non-transparent can be rotated out of the sphere of influence of components of the second modality.

Finally the invention relates also to a combination device having a magnetic resonance scanner according to the invention and a second, diagnostic and/or therapeutic modality. The previous statements made can, of course, be applied analogously in this case too. The second modality can be in particular a modality based on beta radiation and/or X-ray radiation.

BRIEF DESCRIPTION OF THE DRAWINGS

Further advantages and details of the present invention will emerge from the exemplary embodiments described herein below as well as with reference to the drawings, in which.

DETAILED DESCRIPTION OF THE INVENTION

Figure 1:
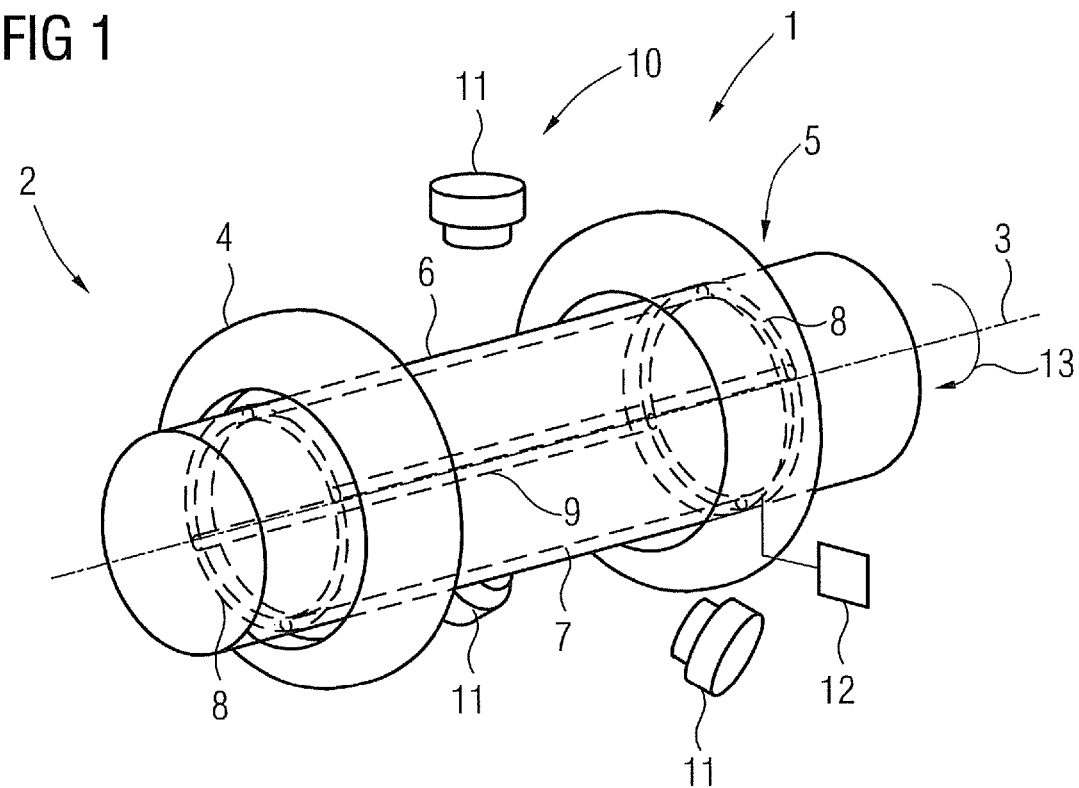
FIG. 1 shows a combination device according to the invention.

FIG. 1 shows the most important components of a combination device 1 according to the invention in a schematic drawing. The combination device 1 according to the invention comprises an inventive open magnetic resonance scanner 2 in the double-doughnut configuration which comprises two coaxial, cylindrical magnet sections 4 spaced apart along a z-direction 3, by means of which a homogeneity volume can be generated in the region of the z-direction 3 between the two magnet sections 4. The homogeneity volume is therefore located in an area that is not blocked by parts of the main field magnet.

The magnetic resonance scanner 2 also comprises a cylindrical whole-body coil arrangement 5 according to the invention which, as can be seen, extends through the bores of the magnet sections 4 and hence covers the formerly open area between the magnet sections 4 with a radio-frequency shield 6. The whole-body coil arrangement 5 additionally comprises coil conductors 7 that are only indicated here. The coil is a birdcage coil having end rings 8 and longitudinal conductors 9 (indicated).

The combination device 1 now further comprises a second modality, in this case an irradiation device 10 having three cobalt emitters 11 that are rotatable in the z-direction 3 and provided for the purpose of generating beta radiation, for treating a tumor, for example.

Let it be noted at this juncture that, self-evidently, any other second modalities are also conceivable subject to appropriate adaptation of the whole-body coil arrangement 5 that is now described in more detail.

In order to enable the irradiation device 10 to be operated jointly with the magnetic resonance scanner 2 in the combination device 1, the whole-body coil arrangement 5 is embodied as essentially transparent and homogenous in its attenuation properties. The beta radiation of the cobalt emitters 11 consequently can penetrate the whole-body coil arrangement 5, in particular the radio-frequency shield 6 and the coil conductors 7, essentially unobstructed and achieve the desired therapeutic effect, so there is no longer any need to dispense with the radio-frequency shield.

However, the whole-body coil arrangement 5 also comprises further elements, for example capacitors, which possibly may not be embodied transparently to the desired extent. Additionally provided in the combination device 1 for this reason is a rotator device 12 by means of which the rotatably mounted whole-body coil arrangement 5 can be rotated about the z-direction 3, arrow 13. Thus, the non-transparent elements can be rotated out of the sphere of influence of the irradiation device 10.

Let it be noted at this juncture that an embodiment variant is, of course, also conceivable in which only the radio-frequency shield 6 is embodied as transparent, the coil conductors 7 being rotated out of the sphere of influence.

Figure 2:
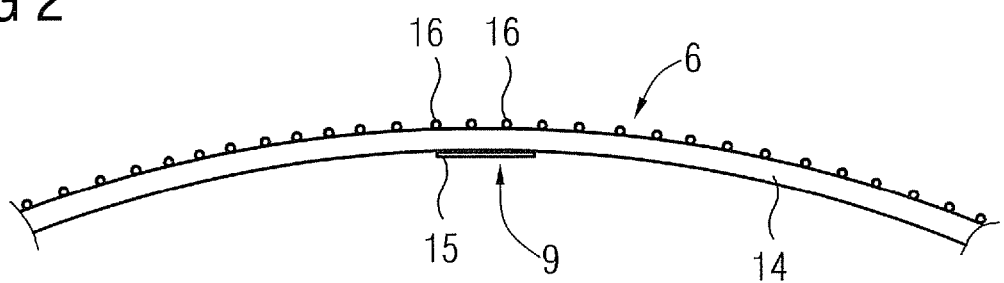
FIG. 2 shows a detail section from a first embodiment variant of the whole-body coil arrangement according to the invention.
Figure 3:
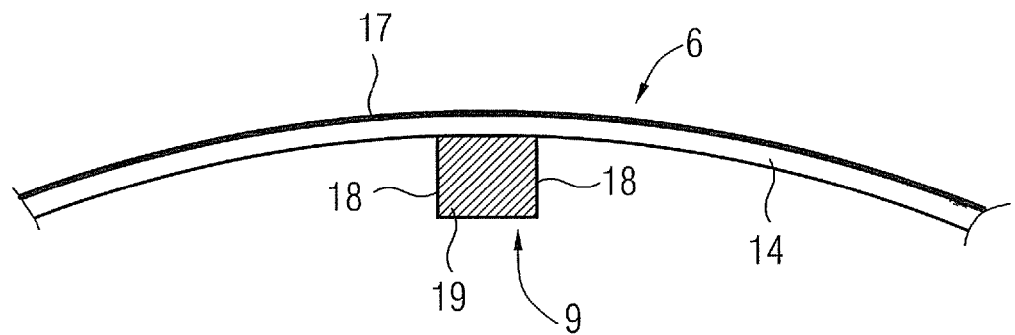
FIG. 3 shows a detail section from a second embodiment variant of a whole-body coil arrangement according to the invention.

FIGS. 2 and 3 show different embodiment variants of the whole-body coil arrangement 5 according to the invention. In the first embodiment variant shown in FIG. 2 a thin carrier element 14 made of plastic is provided which has a low density and so is already essentially transparent per se. On the inside of the cylindrical carrier element 14 the conductor tracks 7, here, in the present example, of a longitudinal conductor 9, are applied as a thin aluminum layer 15. The radio-frequency shield 6 is applied on the opposite side as a micromesh or fine-meshed grid 16, likewise made of aluminum. The fine-meshed grid 6 even permits optical transparency in the visible range, for which reason in this first embodiment variant the carrier element 14 is also embodied as transparent in the visible range.

FIG. 3 shows a second embodiment variant in which once again a cylindrical carrier element 14 is provided, of which, here too, only a detail section is shown. In contrast to the first embodiment variant the radio-frequency shield 6 is formed in this case likewise by means of a continuous, thin aluminum layer 17.

In the second embodiment variant the longitudinal conductor 9 shown in cross-section is composed of a plurality of extremely thin aluminum layers 18. They are arranged in such a way that they form a square cross-section. In this way very thin layers can be used to form a conductor that nonetheless has sufficient conductivity. The structure of the longitudinal conductor 9 is supported by means of a material 19 of very low density, cellular material for example.

Needless to say, other embodiments by means of which coil conductors of extremely thin layer thickness can be produced are also conceivable.

Finally let it be noted also that other modalities apart from the irradiation device 10 can, of course, also be used as the second modality, as already discussed.

In addition to the embodiment variants illustrated in FIG. 2 and FIG. 3 it is also possible to create a whole-body coil arrangement 5 that is transparent to ultrasound, if a membrane capable of oscillation is used as the carrier element 14.

The invention claimed is:

1. A whole-body coil arrangement for an open magnetic resonance scanner for use with a second diagnostic and/or therapeutic modality, comprising:
   a coil conductor;
   spaced-apart magnet sections;
   a radio-frequency shield extending through bores of the spaced apart magnet sections that covers an open area between the spaced apart magnet sections; and
   a plastic cylindrical carrier element;
   wherein the coil conductor is constructed from a metal layer applied to an inside surface of the carrier element, wherein a thickness of the metal layer is chosen according to a penetration depth of the second diagnostic and/or therapeutic modality;
   wherein the radio-frequency shield is at least partially a fine-meshed grid and is applied to a surface of the carrier element opposite the inside surface;
   wherein the coil conductor and/or the radio frequency shield consists of aluminum;
   wherein the second diagnostic and/or therapeutic modality comprises an emitter for generating radiations, and
   wherein the whole-body coil arrangement is configured to be at least partially transparent in the open area such that the whole-body coil arrangement is penetrable by the radiations generated by the second diagnostic and/or therapeutic modality.

2. The whole-body coil arrangement as claimed in claim 1, wherein the whole-body coil arrangement is configured to be transparent in the open area of the open magnetic resonance scanner.

3. The whole-body coil arrangement as claimed in claim 1, wherein the whole-body coil arrangement is configured to be essentially transparent.

4. The whole-body coil arrangement as claimed in claim 1, wherein an attenuation property of the whole-body coil arrangement is homogenous in the transparent area.

5. The whole-body coil arrangement as claimed in claim 1, wherein the whole-body coil arrangement is a cylinder comprising two cylindrical and/or rectangular coaxial magnet sections.

6. The whole-body coil arrangement as claimed in claim 1, further comprising a rotator for rotating the whole-body coil arrangement so that the coil conductor is rotated out of influence of the second diagnostic and/or therapeutic modality.

7. An open magnetic resonance scanner, comprising:
   spaced apart magnet sections; and
   a whole-body coil arrangement for use with a second diagnostic and/or therapeutic modality comprising an emitter for generating radiations, the whole-body coil arrangement comprising:
   a coil conductor;

a radio-frequency shield extending through bores of the spaced apart magnet sections of the open magnetic resonance scanner that covers an open area between the spaced apart sections; and a plastic cylindrical carrier element;

wherein the coil conductor is constructed from a metal layer applied to an inside surface of the carrier element, wherein a thickness of the metal layer is chosen according to a penetration depth of the second diagnostic and/or therapeutic modality;

wherein the radio-frequency shield is at least partially a fine-meshed grid and is applied to a surface of the carrier element opposite the inside surface;

wherein the coil conductor and/or the radio frequency shield consists of aluminum;

wherein the whole-body coil arrangement is configured to be at least partially transparent in the open area such that the whole-body coil arrangement is penetrable by the radiations generated by the second diagnostic and/or therapeutic modality.

8. The open magnetic resonance scanner as claimed in claim 7, wherein the whole-body coil arrangement is mounted to be rotatable.

9. The open magnetic resonance scanner as claimed in claim 7, wherein the whole-body coil arrangement is a cylinder.

10. A medical device, comprising:
an open magnetic resonance scanner comprising a whole-body coil arrangement and spaced apart magnet sections, the whole-body coil arrangement comprising:
a coil conductor,
a radio-frequency shield extending through bores of the spaced apart magnet sections of the open magnetic resonance scanner that covers an open area between the spaced apart magnet sections; and
a plastic cylindrical carrier element;
wherein the coil conductor is constructed from a metal layer applied to an inside surface of the carrier element;
wherein the radio-frequency shield is at least partially a fine-meshed grid and is applied to a surface of the carrier element opposite the inside surface;
wherein the coil conductor and/or the radio frequency shield consists of aluminum; and
a second diagnostic and/or therapeutic modality comprising an emitter for generating radiations, wherein a thickness of the metal layer is chosen according to a penetration depth of the second diagnostic and/or therapeutic modality,
wherein the whole-body coil arrangement is configured to be at least partially transparent in the open area such that the whole-body coil arrangement is penetrable by the radiations generated by the second diagnostic and/or therapeutic modality.

11. The medical device as claimed in claim 10, wherein the second modality is a beta radiation modality and/or an X-ray radiation modality.

* * * * *